United States Patent
Nichols

[11] Patent Number: 5,989,251
[45] Date of Patent: Nov. 23, 1999

[54] APPARATUS FOR SPINAL STABILIZATION

[75] Inventor: David Nichols, Trumbull, Conn.

[73] Assignee: Surgical Dynamics, Inc., Norwalk, Conn.

[21] Appl. No.: 09/098,607

[22] Filed: Jun. 17, 1998

[51] Int. Cl.⁶ .................................................. A61B 17/58
[52] U.S. Cl. .............................................................. 606/61
[58] Field of Search ................................ 606/61, 60, 72, 606/73; 623/17

[56] References Cited

U.S. PATENT DOCUMENTS

| | | |
|---|---|---|
| 4,269,178 | 5/1981 | Keene . |
| 4,641,636 | 2/1987 | Cotrel . |
| 4,815,453 | 3/1989 | Cotrel . |
| 4,887,596 | 12/1989 | Sherman . |
| 5,010,879 | 4/1991 | Moriya et al. . |
| 5,074,864 | 12/1991 | Cozad et al. . |
| 5,084,049 | 1/1992 | Asher et al. . |
| 5,102,412 | 4/1992 | Rogozinski . |
| 5,112,332 | 5/1992 | Cozad et al. . |
| 5,116,334 | 5/1992 | Cozad et al. . |
| 5,181,917 | 1/1993 | Rogozinski . |
| 5,261,912 | 11/1993 | Frigg . |
| 5,275,600 | 1/1994 | Allard et al. . |
| 5,281,222 | 1/1994 | Allard et al. . |
| 5,312,405 | 5/1994 | Korotko et al. . |
| 5,334,203 | 8/1994 | Wagner . |
| 5,346,493 | 9/1994 | Stahurski et al. . |
| 5,360,431 | 11/1994 | Puno et al. . |
| 5,368,594 | 11/1994 | Martin et al. . |
| 5,380,326 | 1/1995 | Lin . |
| 5,437,671 | 8/1995 | Lozier et al. . |
| 5,439,463 | 8/1995 | Lin . |
| 5,479,462 | 12/1995 | Allard et al. . |
| 5,496,321 | 3/1996 | Puno et al. . |
| 5,498,263 | 3/1996 | DiNello et al. . |
| 5,507,746 | 4/1996 | Lin . |
| 5,520,688 | 5/1996 | Lin . |
| 5,549,607 | 8/1996 | Olsen et al. . |
| 5,562,663 | 10/1996 | Wisnewski et al. . |
| 5,601,554 | 2/1997 | Howland et al. . |
| 5,624,440 | 4/1997 | Huebner . |
| 5,624,442 | 4/1997 | Mellinger et al. . |
| 5,630,817 | 5/1997 | Rokegem et al. . |
| 5,667,506 | 9/1997 | Sutterlin . |
| 5,667,507 | 9/1997 | Corin et al. . |
| 5,669,910 | 9/1997 | Korhonen et al. . |
| 5,676,665 | 10/1997 | Bryan . |
| 5,683,390 | 11/1997 | Metz-Stavenhagen et al. . |
| 5,688,272 | 11/1997 | Montague et al. . |
| 5,693,053 | 12/1997 | Estes . |
| 5,702,393 | 12/1997 | Pfaifer . |
| 5,702,395 | 12/1997 | Hopf . |
| 5,707,372 | 1/1998 | Errico et al. . |
| 5,709,684 | 1/1998 | Errico et al. . |
| 5,709,685 | 1/1998 | Dombrowski et al. . |

FOREIGN PATENT DOCUMENTS

| | | |
|---|---|---|
| 0553042 | 1/1993 | European Pat. Off. . |
| 0811357 | 8/1997 | European Pat. Off. . |

*Primary Examiner*—Michael Buiz
*Assistant Examiner*—Jonathan Goldberg

[57] ABSTRACT

An apparatus is disclosed for connecting first and second elongated spaced apart spinal rods to one another which includes a first connector having structure to engage a first spinal rod at a location along the length thereof and an elongated beam having an axis extending in a direction transverse to the first spinal rod, a second connector having structure to engage a second spinal rod at a location adjacent the first connector and including a reception portion projecting in a direction transverse to the second spinal rod and defining a channel for receiving the elongated beam of the first connector, and a locking member dimensioned and configured to engage the channel along the axis of the beam and secure the position of the beam with respect thereto.

31 Claims, 8 Drawing Sheets

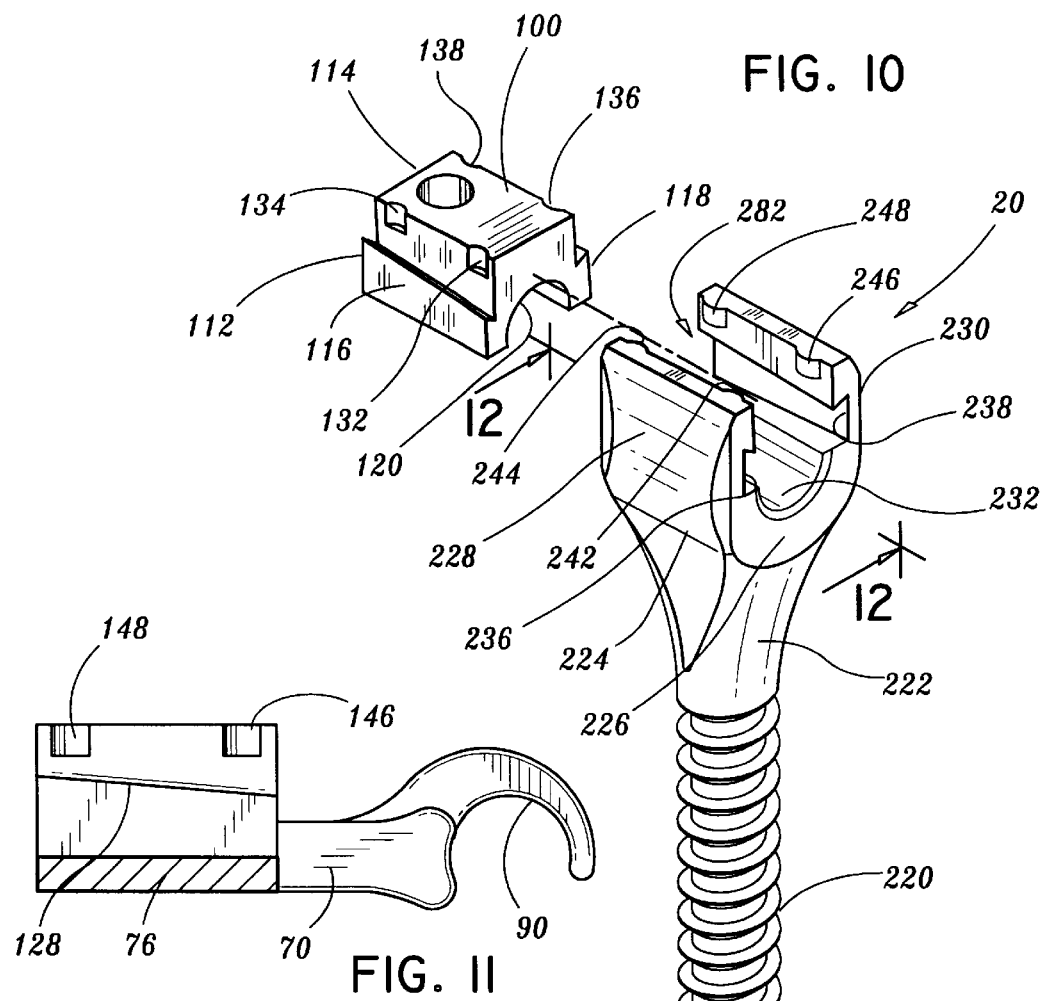
FIG. 10
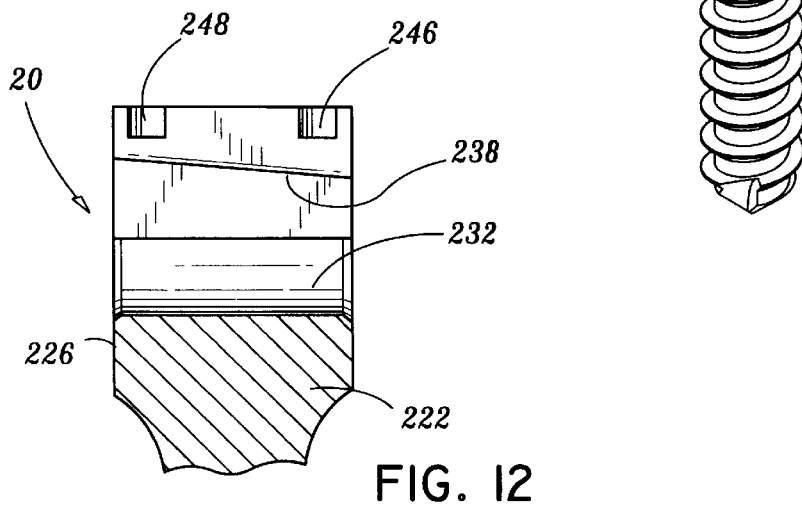
FIG. 11
FIG. 12

APPARATUS FOR SPINAL STABILIZATION

BACKGROUND OF THE INVENTION

1. Field of the Invention

The subject disclosure relates to implantable spinal stabilization systems for surgical treatment of spinal disorders, and more particularly, to an apparatus for connecting cylindrical spinal rods of a spinal stabilization system to one another across the spinous process.

2. Background of the Related Art

The spinal column is a complex system of bones and connective tissue which protects critical elements of the nervous system. Despite these complexities, the spine is a highly flexible structure, capable of a high degree of curvature and twist through a wide range of motion. Trauma or developmental irregularities can result in spinal pathologies which limit this range of motion.

For many years, orthopedic surgeons have attempted to correct spinal irregularities and restore stability to traumatized areas of the spine through immobilization. Over the past ten years, spinal implant systems have been developed to achieve immobilization. Examples of such systems are disclosed in U.S. Pat. Nos. 5,102,412 and 5,181,917. Such systems often include spinal instrumentation having connective structures such as elongated rods which are placed on opposite sides of the portion of the spinal column intended to be immobilized. Screws and hooks are commonly utilized to facilitate segmental attachment of such connective structures to the posterior surfaces of the spinal laminae, through the pedicles, and into the vertebral bodies. These components provide the necessary stability both in tension and compression to achieve immobilization.

It has been found that when a pair of spinal rods are fastened in parallel on either side of the spinous process, the assembly can be significantly strengthened by using at least one additional rod to horizontally bridge the pair of spinal rods. An example of a cross brace assembly of this type is disclosed in U.S. Pat. No. 5,084,049. Devices such as these commonly consist of a threaded rod for providing the desired lateral support. The threaded rod is fastened to each of the spinal rods by clamps located on each end thereof. However, this configuration is bulky and can cause irritation of the patient's back muscles and other tissue which might rub against the device. A cross brace assembly that fits closer to the spine, preferably in the same general plane as the cylindrical spinal rods, would reduce the complications associated with bulkier devices.

Most existing transverse connectors consist of rods, plates, and bars linked to the longitudinal rods by coupling mechanisms with set screws, nuts, or a combination of each. These connectors require several components and instruments to build the constructs. Each additional component or instrument required to assemble the connectors adds to the complexity of the surgical procedure. Examples of connectors constructed from multiple components are disclosed in U.S. Pat. Nos. 5,312,405, 5,334,203 and 5,498,263.

It would be beneficial to provide an improved device to transversely connect spinal rods of a spinal stabilization system to one another which utilizes a minimum number of components parts and which reduces the posterior horizontal profile and overall bulkiness of the system.

SUMMARY OF THE DISCLOSURE

The subject disclosure is directed to an apparatus for connecting two spinal rods of a spinal stabilization system to one another in such a manner so as to provide an adjustable low-profile rigid linkage there between. The apparatus disclosed herein includes a first connector having a pair of opposed spaced apart arcuate engaging members associated therewith for engaging a first elongated spinal rod at a location along the length thereof. The first connector further includes an elongated connective beam which extends in a direction transverse to the first spinal rod to form a bridge across the spinous process.

The apparatus further includes a second connector having a pair of opposed spaced apart arcuate engaging members associated therewith for engaging a second spinal rod at a location adjacent the first connector. The second connector includes a reception portion which projects in a direction transverse to the second spinal rod and defines a channel for receiving the elongated beam of the first connector. The apparatus further includes a locking member which is dimensioned and configured to linearly engage the channel and positively secure the position of the elongated beam with respect thereto.

The channel of the reception portion is preferably defined by a base portion having a planar surface and a pair of opposed spaced apart upstanding side walls. The elongated beam preferably has a semi-circular transverse cross-section, with a lower surface thereof being planar and an upper surface thereof being arcuate. In this embodiment, when the apparatus is installed, the planar lower surface of the elongated beam is disposed in face-to-face contact with the planar surface of the base portion of the reception channel. The locking member preferably includes a lower body portion having a lower surface with an hemi-cylindrical channel for accommodating the upper arcuate surface of the elongated beam.

In addition, the locking member preferably includes a mechanism designed to provide secure fixation of the elongated connective beam of the first connector within the reception channel of the second connector. The mechanism is defined in part by a pair of laterally opposed tapered wedges configured to engage complementary tapered slots defined in the opposed spaced apart upstanding side walls of the reception channel.

The mechanism is preferably further defined by a pair of reception ports located on each of the lateral sides of the upper body portion of the locking member. The reception ports are spaced above the tapered wedges and are positioned at locations adjacent the opposed leading and trailing ends of the upper body portion of the locking member. The locking tabs are configured to positively receive and engage corresponding complementary locking tabs projecting from the interior surfaces of the opposed spaced apart upstanding side walls of the reception channel.

Because the tapered wedges of the locking member engage the slots of the reception channel linearly along the axis of the elongated connective beam, the application of undesirable torsional forces to the spine normally generated during the process of tightening a conventional threaded component is avoided. Moreover, while threaded components can loosen under cyclically applied loads commonly encountered by the spinal column, the secure locking mechanism of the locking member remains fixed under such conditions.

The subject disclosure is also directed to a connecting member for connecting a transverse spinal rod to a longitudinal spinal rod comprising a base portion, a pair of spaced apart arcuate engaging members extending in a first direction from the base portion to engage the longitudinal spinal rod, and a pair of upstanding walls extending in a direction transverse to the first direction and forming a channel therebetween to receive the transverse spinal rod.

The subject disclosure is also directed to a connecting member for connecting a transverse spinal rod to a longitudinal spinal rod comprising a base portion, a pair of upstanding walls extending from the base portion forming a channel to receive a transverse spinal rod in a first plane, and a pair of arcuate engaging members extending from the base portion to engage the longitudinal rod in substantially the same plane as the first plane.

A system for spinal stabilization is also disclosed comprising first and second elongated spinal rods, at least one fastening device for securing the first and second spinal rods to first and second sides of the spine, first and second connectors for engaging the spinal rods, and a locking member to secure a connective beam of the first connector to the second connector as described herein.

These and other features of the apparatus disclosed herein and the method of installing the same will become more readily apparent from the following description of the drawings.

BRIEF DESCRIPTION OF THE DRAWINGS

So that those having ordinary skill in the art to which the disclosed apparatus appertains will more readily understand how to construct and use the same, reference may be had to the drawings wherein:

FIG. 10 is a perspective view of a bone screw constructed in accordance with a preferred embodiment of the subject disclosure which is employed with the spinal stabilization system illustrated in FIG. 1, and which includes a locking member as used in conjunction with the connector of FIG. 5; and FIG. 11 is a cross-sectional view taken along line 11—11 of FIG. 5 illustrating the locking features of the second rod connector component;

FIG. 12 is a cross-sectional view taken along line 12—12 of FIG. 10 illustrating the locking features of the bone screw.

These and other features of the apparatus disclosed herein will become more readily apparent to those having ordinary skill in the art from the following detailed description taken in conjunction with the drawings.

DETAILED DESCRIPTION OF THE PREFERRED EMBODIMENTS

Figure 1:
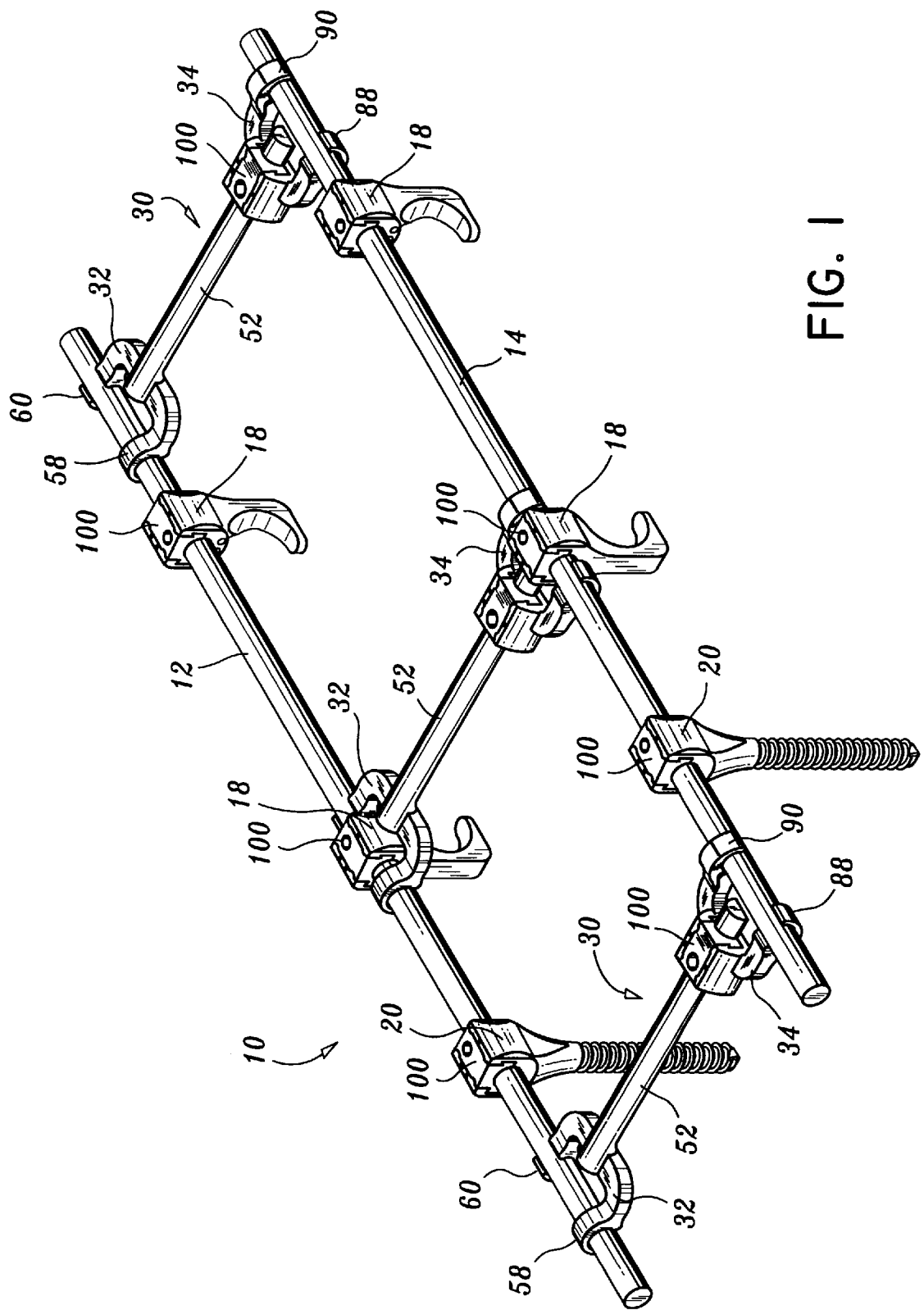
FIG. 1 is a perspective view of a spinal stabilization system for immobilizing a region of the spinal column which includes rod connecting apparatus constructed in accordance with a preferred embodiment of the subject disclosure.

Referring now to the drawings wherein like reference numerals identify similar structural elements of the subject apparatus, there is illustrated in FIG. 1 a spinal stabilization system constructed in accordance with a preferred embodiment of the subject disclosure and designated generally by reference numeral 10.

Figure 2:
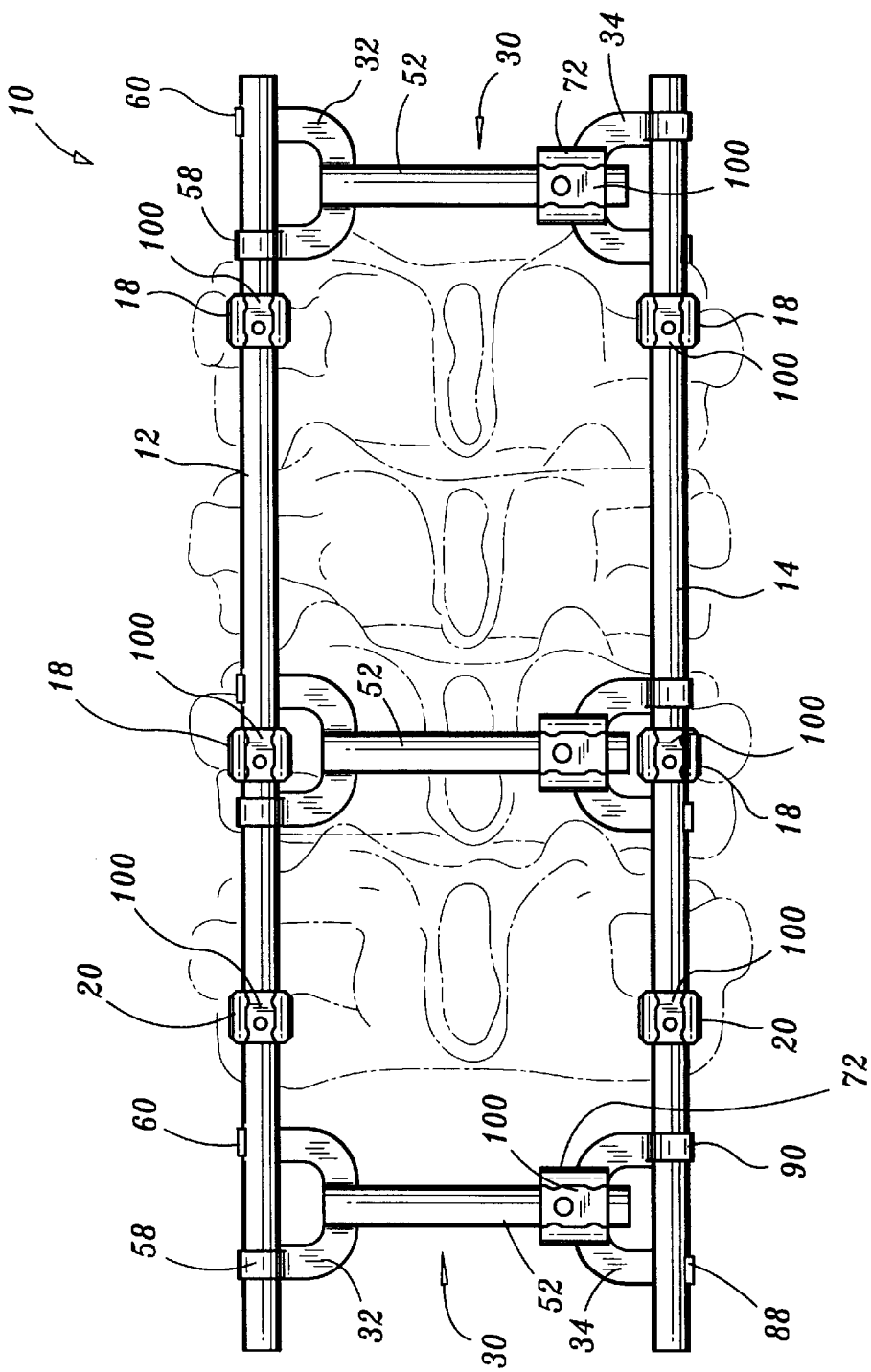
FIG. 2 is a top plan view of the spinal stabilization system of FIG. 1 implanted on the posterior side of the spinal column.
Figure 3:
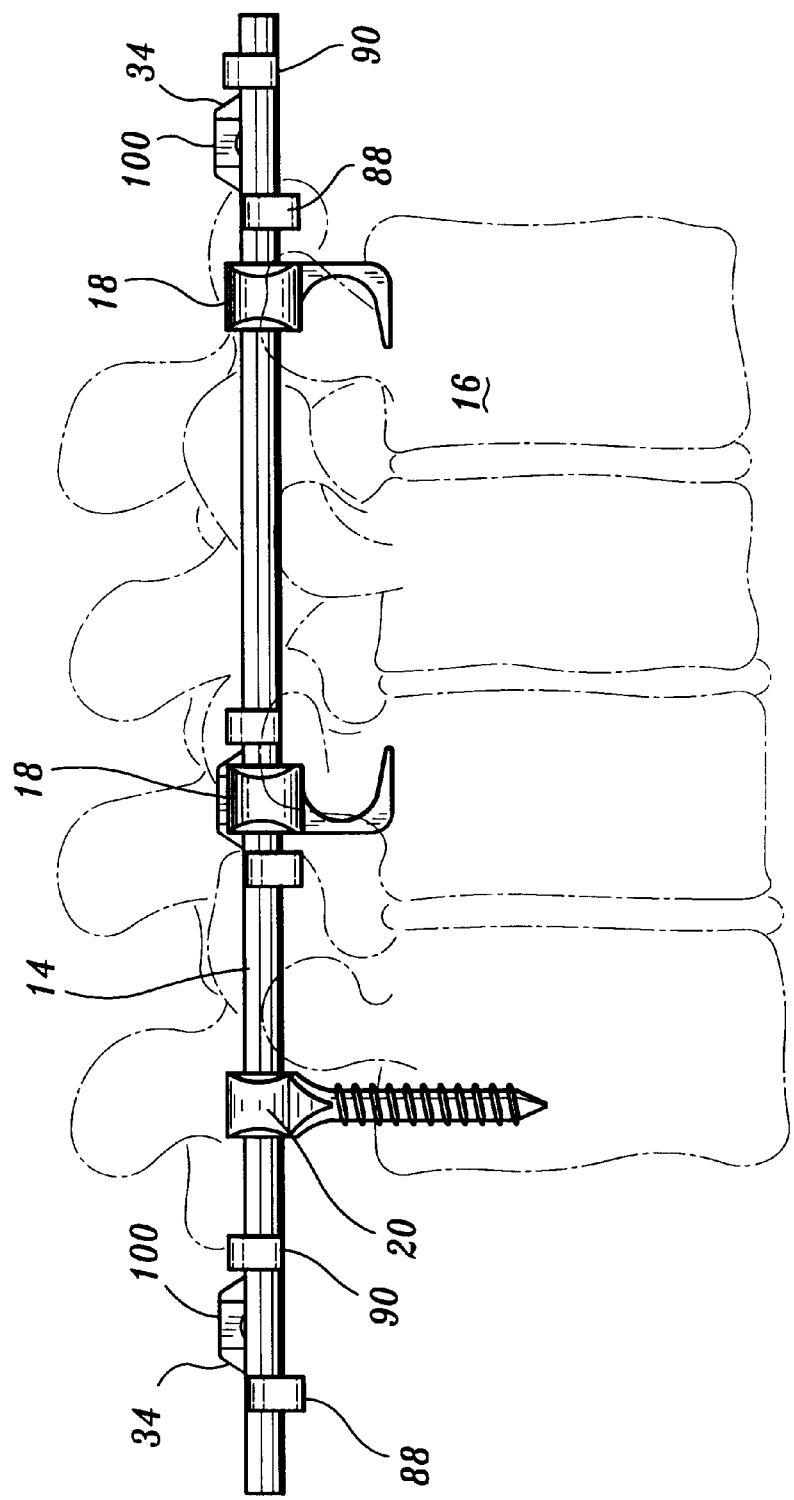
FIG. 3 is a side elevational view of the spinal stabilization system of FIG. 1 implanted on the posterior side of the spinal column.

Referring to FIG. 1. in conjunction with FIGS. 2 and 3, stabilization system 10 includes a pair of elongated (longitudinal) spinal rods 12 and 14 deployed in parallel on either side of the spinous process 16. Spinal rods 12 and 14 are of a conventional type, constructed from a biocompatible material and having a circular cross-section with a smooth outer surface finish. Spinal rods 12 and 14 are segementally secured to the bones of the spine by a variety of different structural components including, for example, spinal hooks 18 and bone screws 20. The construction of bone screw 20 and hook 18 will be described in greater detail hereinbelow with specific reference to FIGS. 11 and 12.

It has been found that when a pair of spinal rods are fastened to one another in parallel on either side of the spine, as illustrated for example in FIGS. 2 and 3, the stabilization system can be significantly strengthened. Thus, the spinal rods 12 and 14 of stabilization system 10 are connected to one another by readily adjustable, low-profile rod linking devices constructed in accordance with a preferred embodiment of the subject disclosure and designated generally by reference numeral 30.

With continuing reference to FIGS. 1 through 3, each rod coupling device 30 includes first and second rod connectors 32 and 34 which are independently engaged to spinal rods 12 and 14, respectively, by a rod engagement mechanism which will be described in detail hereinbelow with reference to FIGS. 4 and 5. In accordance with the subject disclosure, the first and second rod connectors 32 and 34 are transversely coupled to one another by a securement mechanism which will also be described in detail hereinbelow.

Figure 4:
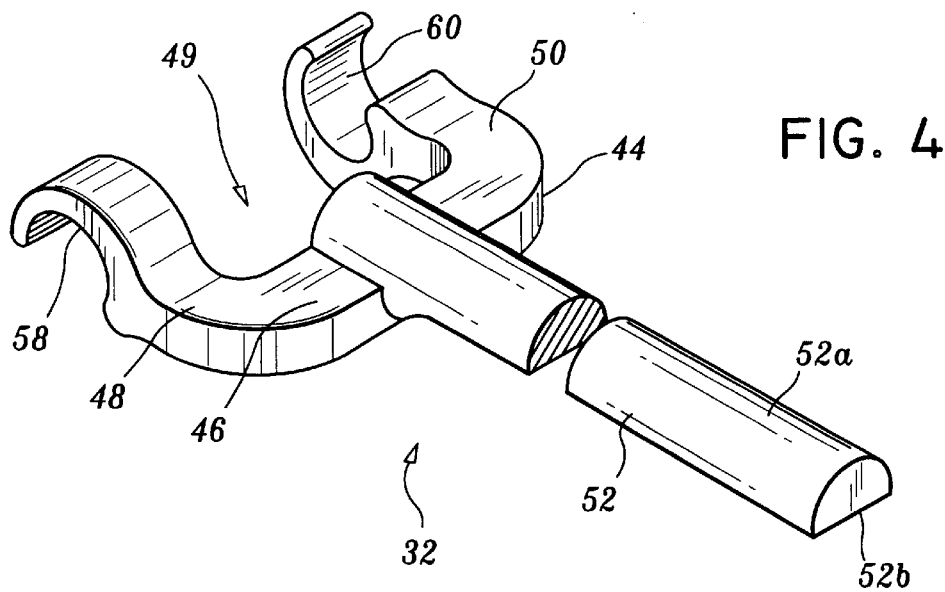
FIG. 4 is a perspective view of a first connector which forms part of the rod connecting apparatus illustrated in FIG. 1.
Figure 5:
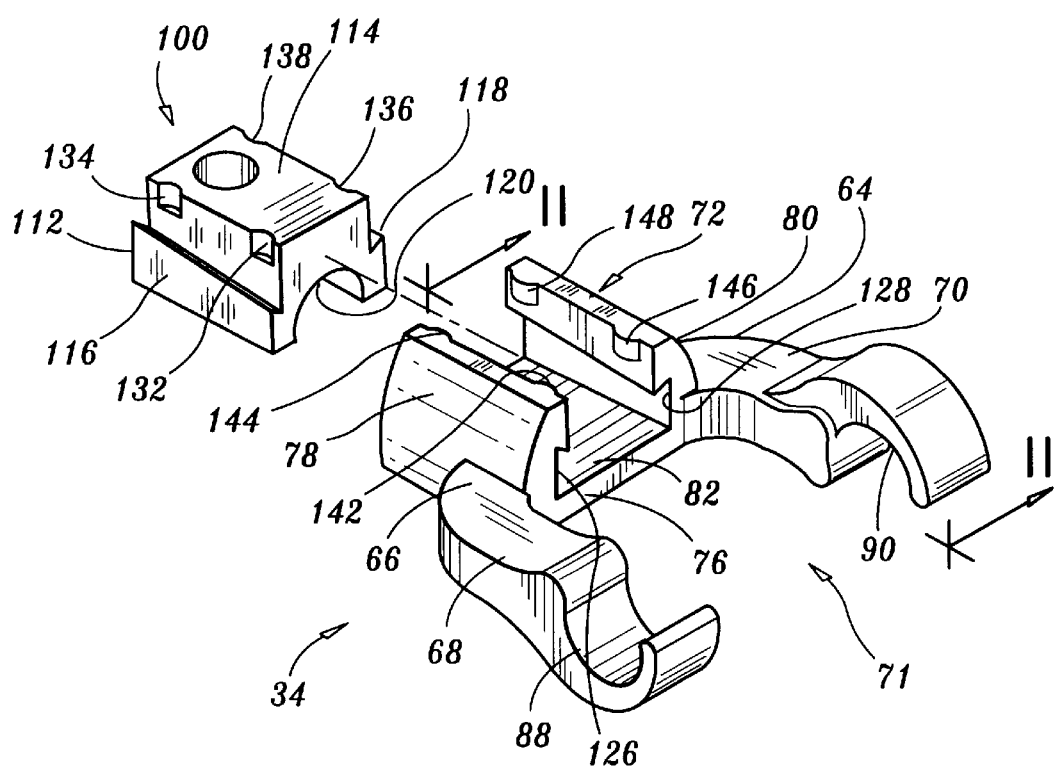
FIG. 5 is a perspective view of a second connector which forms part of the rod connecting apparatus illustrated in FIG. 1, together with the locking member operatively associated therewith.

Referring now to FIGS. 4 and 5, there are illustrated each of the components which define the rod coupling device 30 of the subject invention. With specific reference to FIG. 4, the first rod connector 32 includes a yoke 44 defined by a base portion 46 and a pair of spaced apart arms 48 and 50 which depend from the base portion and define a gap 49 therebetween. An elongated connective beam 52 depends from base portion 46 in a direction opposite the pair of spaced apart arms 48 and 50 to traverse the spinous process. Connective beam 52 preferably has a semi cross-sectional configuration defined by an arcuate upper surface 52a and a planar lower surface 52b. Oppositely facing mirror-image rod engaging structures 58 and 60 having the form of arcuately shaped clips (see also FIG. 11) depend from the ends of arms 48 and 50, respectively, for securely clamping the first connector 32 to spinal rod 12 during a spinal stabilization procedure.

Figure 4A:
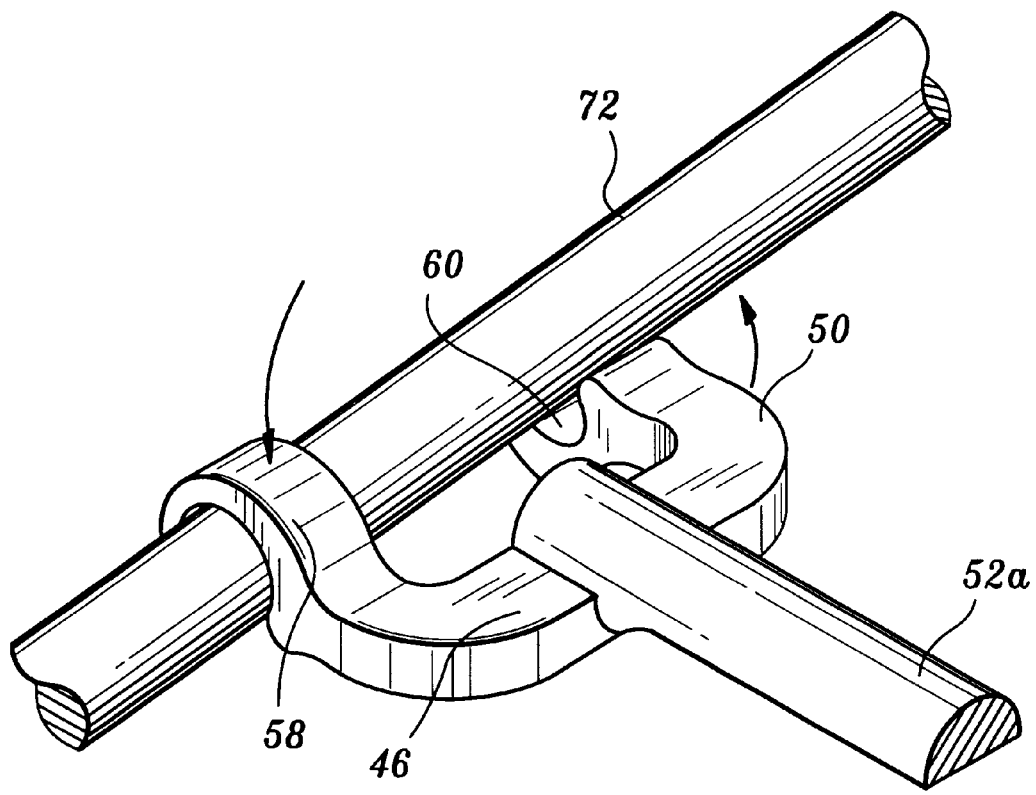
FIG. 4A is a perspective view of the first connector showing its rotation to clamp onto the longitudinal rod of the spinal stabilization system.

The arcuate rod engaging structures or clips 58 and 60 each have an inner diameter that is slightly less than the outer diameter of spinal rod 12. During installation of connector device 30, rod connector 32 is first positioned so that longitudinal rod 12 lies in gap 49 and clips 58 and 60 are on opposite sides of the rod 12. Then, connector 32 is rotated relative to spinal rod 12 (see FIG. 4A), causing deflection of the depending arms 48 and 50 and diametrical expansion or spreading of the arcuate rod engaging clips 58 and 60 which facilitates clamping of connector 32 onto spinal rod 12.

Referring to FIG. 5, there is illustrated the second connector 34 of rod linking device 30 which includes a yoke 64 defined by a base portion 66 and a pair of spaced apart arms 68 and 70 which depend from the base portion and define a gap 70 therebetween. A reception portion 72 projects from the base portion 66 of yoke 64 in a direction orthogonal to the direction of the pair of spaced apart arms 68 and 70 to receive the free end of connective beam 52 when it traverses the spine. Reception portion 72 is defined by a base 76 and a pair of opposed spaced apart upstanding walls 78 and 80 which extend transverse to both the base portion 66 and arms 68 and 70 and which delineate a linear channel 82 therebetween. Oppositely facing mirror-imaged rod engaging structures 88 and 90 having the form of arcuately shaped clips depend from the ends of arms 68 and 70, respectively, for securely clamping the second connector 34 to spinal rod 14 during a surgical procedure.

As described hereinabove with respect to connector 32, the arcuate rod engaging structures or clips 88 and 90 of second connector 34 each have an inner diameter that is slightly less than the outer diameter of spinal rod 14. During installation, rotation of connector 34 relative to spinal rod 14 causes the deflection of depending arms 68 and 70 and the diametrical expansion or spreading of the arcuate rod engaging clips 88 and 90 which facilitates clamping of connector 34 onto spinal rod 14.

With continuing reference to FIG. 5, rod linking device 30 further includes a locking member 100 having a lower portion 112 and an upper portion 114. The lower portion 112 includes a pair of laterally opposed tapered wedges 116 and 118 defined by a construct which employs an inwardly angled sloping locking surface. The tapered wedges 116 and 118 are dimensioned and configured to linearly engage correspondingly configured slots 126 and 128 defined in upstanding walls 78 and 80. (see FIG. 11). The lower portion 112 of locking member 100 further includes a hemi-cylindrical channel 120 extending along the longitudinal axis thereof for accommodating the arcuate upper surface of 52*a* of connective beam 52 when it traverses the spinous process and is received by the reception portion 72 of the second connector 34. At such a time, the planar lower surface 52*b* of connective beam 52 is in face-to-face contact with the planar surface of the base 76 of reception portion 72.

With continuing reference to FIG. 5 in conjunction with FIG. 11, the upper portion 114 of locking member 100 further includes a provisional securement (locking) mechanism consisting of laterally opposed paired retention ports 132, 134 and 136, 138. Laterally opposed retention ports 132 and 136 are disposed adjacent the leading end of locking member 100 while laterally opposed retention ports 134 and 138 are disposed adjacent the trailing end of locking member 100. The paired retention ports are dimensioned and configured to receive and securely retain corresponding paired engagement tabs 142, 144 and 146, 148 which project into the linear channel 82 from the opposed upstanding side walls 78 and 80 of reception portion 72. This provisional locking maintains the locking member 18 in place until it is fully locked upon full engagement of tapered wedges 116, 118 and slots 126, 128.

Turning now to the hooks and screws for connecting spinal rods 12 and 14 to the vertebrae, and referring first to FIG. 10, there is illustrated a bone screw designated generally by reference numeral 20. Bone screw 20 includes a lower threaded portion 220 for fastening the screw to the spinous process, an intermediate shank portion 222 having a smooth outer surface which tapers radially outwardly from the circumference of the lower threaded portion 220, and an upper body portion 224. Threaded portion 220 of bone screw 20 is provided with a helical thread designed to easily penetrate and securely engage the bone to fix the longitudinal rods 12 and 14 with respect to the vertebrae. The upper body portion 224 of bone screw 20 is defined by a base 226 and a pair of opposed upstanding side walls 228 and 230 which define a linear channel 282 therebetween. A hemi-cylindrical channel 232 is formed in the base 226 of body portion 224 for accommodating the lower portion of an elongated spinal rod 12, 14 received by the body portion 224.

With continuing reference to FIG. 10, bone screw 20 is provided with a locking member 100 which, as discussed hereinabove with reference to FIG. 5, includes a pair of laterally opposed tapered wedges 116 and 118 configured to linearly engage correspondingly configured slots 236 and 238 defined in the upstanding side walls 228 and 230 of body portion 224 (see FIG. 12). As described hereinabove with respect to FIG. 5, the upper portion 114 of locking member 100 includes a provisional securement mechanism consisting of laterally opposed spaced apart paired retention ports 132, 134 and 136, 138, which are dimensioned and configured to receive and securely retain corresponding spaced apart paired engagement tabs 242, 244 and 246, 248 which project into the linear channel 282 from the opposed upstanding side walls 228 and 230 (see FIG. 12). As discussed hereinabove, the lower portion 112 of locking member 100 includes a hemi-cylindrical channel 120 extending along the longitudinal axis thereof. When used in conjunction with bone screw 20, channel 120 accommodates the upper portion of the spinal rod with which bone screw 20 is associated. Thus, it can be appreciated that preferably the same locking member configuration can be used to secure the bone screw and the connector to the spinal rods 12, 14.

As discussed hereinabove with reference to FIG. 1, in addition to the connective device 30 and bone screws 20, stabilization system 10 also includes hooks 18 for facilitating segmental attachment of spinal rods 12 and 14 to different areas of the spinous process in conjunction with bone screws 20. Because the spine features different laminar geometries, spinal hooks are available in a variety of different configurations including for example, up angled hooks, down angled hooks, pedicle hooks, and neutral hooks.

The spinal hooks 18 which are illustrated in FIG. 1 are configured as lamina hooks and are provided with a locking member 100. The locking member for securing the hooks to the spinal rods is identical to the aforedescribed locking member for the bone screw 20. Locking member 100 linearly engages a corresponding linear channel formed in the upper body of the lamina hook, in the same manner as in connector device 30 and bone screw 20, so as to secure the hook to the spinal rod with which it is associated. (The upper body portion of the hook is identical to the upper body portion 224 of bone screw 20 and therefore is not illustrated in detail.) In accordance with the subject application, it should be understood that locking member 100 can also be employed with up angled hooks, down angled hooks, neutral hooks and other configurations for securement to the spine.

Thus, as noted above, each component of the spinal stabilization system disclosed herein and illustrated in FIGS. 1 through 3 preferably utilizes identically configured locking members. Also, because the tapered wedges of the locking members are configured for linear engagement, undesirable torsional forces normally encountered with threaded components are not applied to the spine during implantation. Also, the linear sliding locking of the locking member provides uniform locking forces and avoids insufficient tightening or overtightening associated with threaded components.

FIG. 1 also illustrates one of the connector devices 30 positioned to straddle spinal hook 18. That is, since the distance between the rod engaging clips 58, 88, 60 and 90 exceeds the width/diameter of the fastener (e.g. hook 18 and bone screw 20), and the base 46, 66 is spaced a sufficient distance from the rod engaging clips, sufficient room is created so that the clips 58, 88 and 60, 90 can optionally be positioned on opposite sides of the hook 18 as shown. This reduces the longitudinal space on the spinal rods 12 and 14 occupied by the components of the stabilization system. The connector 30 can similarly is positioned to span the head of the bone screw 20.

During a spinal stabilization procedure, once the parallel spinal rods 12 and 14 have been securely fastened along either side of the spinous processes, the stabilization system 10 can be significantly strengthened by transversely linking the two spinal rods 12 and 14 to one another with one or more of the connective devices 30. To accomplish transverse rod linking, the first connector 32 of connector device 30 is attached to spinal rod 12 by orienting the spaced apart arms 48 and 50 of yoke 44 so that the spinal rod 12 is disposed within the gap 49 defined therebetween. Connector 32 is then rotated relative to the spinal rod 12, utilizing a surgical instrument, in such a manner so as to cause the opposed arcuate engagement clips 58 and 60 to positively engage spinal rod 12 by spreading around the spinal rod through diametrical expansion. At such a time, the elongated connective beam 52 of connector 32 extends from spinal rod 12, across the spinous process, in such a manner so that the plane defined by the lower surface 52b of connective beam 52 is aligned with the longitudinal axis of spinal rod 12, contributing to the low-profile construction of the device. In other words, when connected, the connective beam 52 and longitudinal spinal rods 12 and 14 lie in substantially the same plane.

Figure 6:
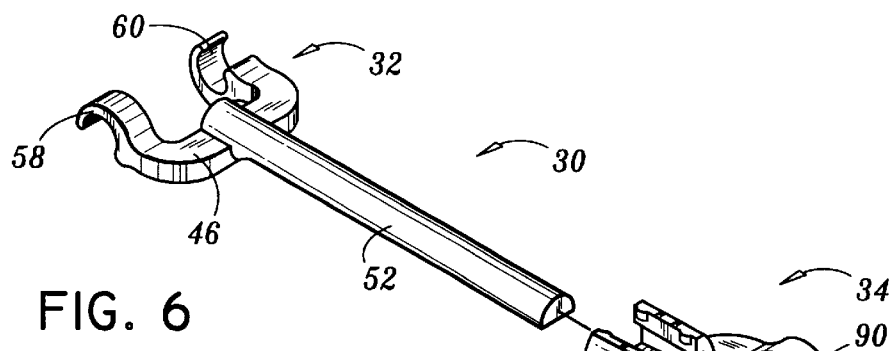
FIGS. 6 through 9 illustrate the sequential operative steps for connectively securing the first and second connector components of the rod connecting device illustrated in FIG. 1 (the longitudinal rods have been omitted for clarity)

Thereafter, the second connector 34 is attached to spinal rod 14 in a similar manner by orienting the spaced apart arms 68 and 70 of yoke 64 so that the spinal rod 14 is disposed within the gap defined therebetween. Connector 34 is then rotated relative to the spinal rod 14, preferably utilizing a surgical instrument, in such a manner so as to cause the opposed arcuate engagement clips 88 and 90 to positively engage spinal rod 14 by spreading around the spinal rod through diametrical expansion. Thereupon, the reception portion 72 projects transversely from spinal rod 14, in such a manner so as to receive the elongate connective beam 52 within reception channel 82, as shown, for example, in FIG. 6. Thus, the beam 52 can be placed between the walls 78 and 80 into the channel 82.

Figure 7:
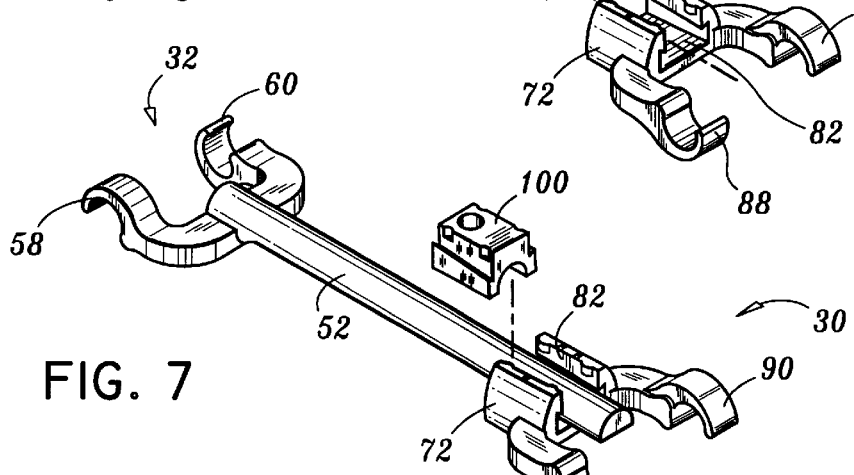
Figure 8:
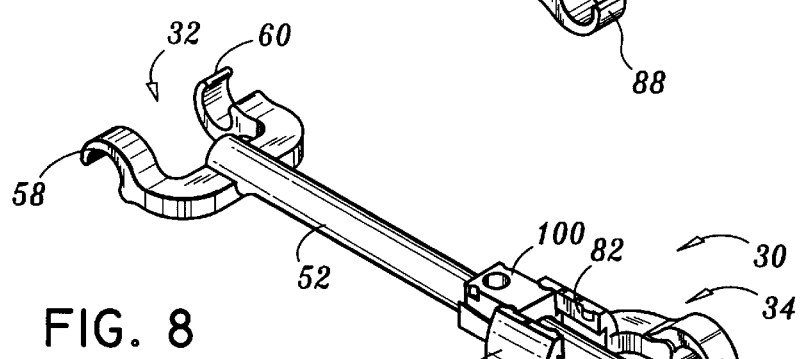
Figure 9:
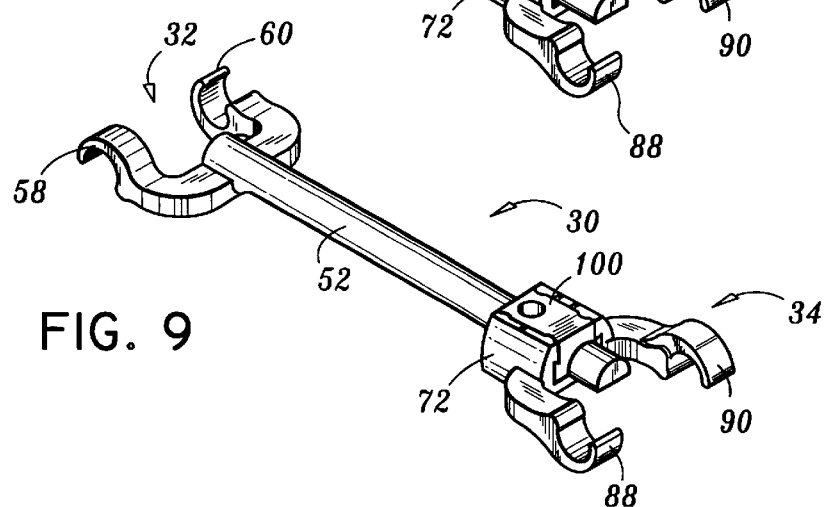

At such a time, the relative positions of the connective beam 52 and the reception channel 82 are properly set by the surgeon, either through rotation of the connectors 32 and 34 about the axes of spinal rods 12 and 14, respectively, or through cutting 52 to the desired length, as shown, for example, in FIG. 7. Locking member 100 is then linearly inserted into reception channel 82 in such a manner so that the opposed tapered wedges 116 and 118 linearly engage the correspondingly configured tapered slots 126 and 128, as shown, for example, in FIG. 8. Linear insertion is continued until such time as the tapered wedges 116, 118 and tapered slots 126, 128 are fully engaged as shown, for example, in FIG. 9. Thereupon, connective beam 52 is securely fastened within reception channel 82 forming a low-profile stable bridge between spinal rods 12 and 14. As illustrated in FIGS. 1 through 3, additional connective devices can be installed to further stabilize apparatus 10.

It should be appreciated that FIG. 1 illustrates the spinal stabilization system with three connecting devices, four hooks and two bone screws by way of example. Clearly, fewer or more of the components can be utilized to construct the stabilization system.

Figure 13:
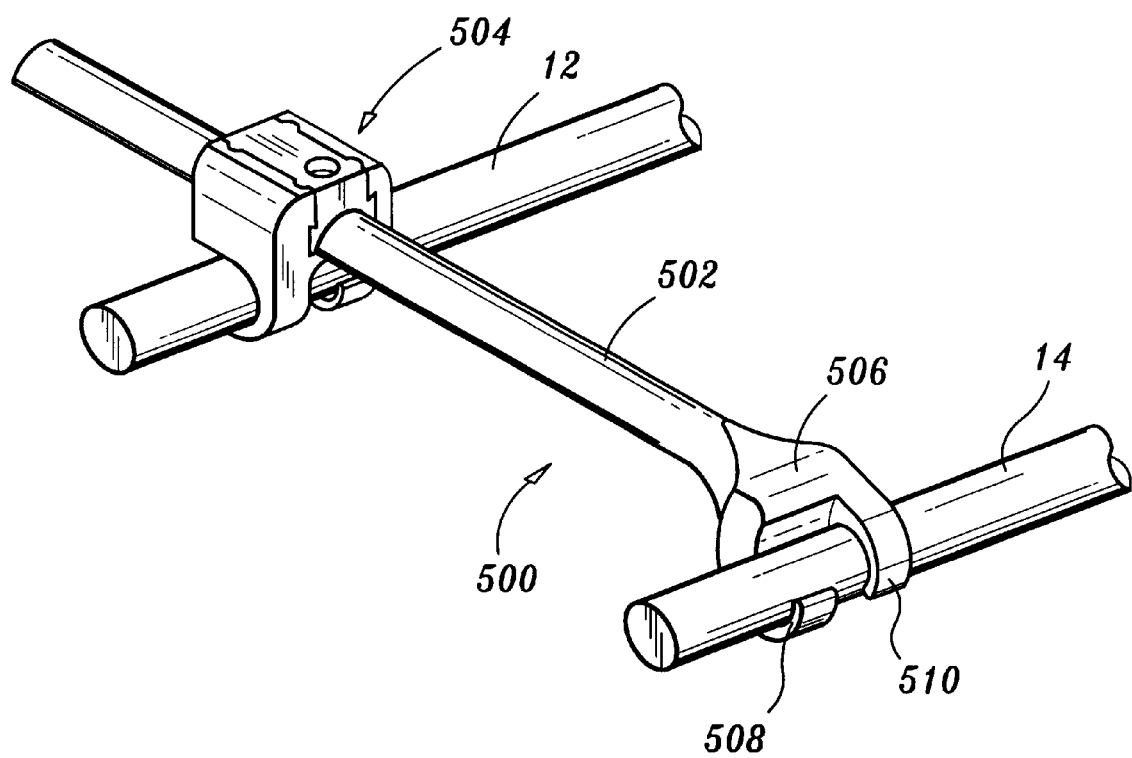
FIG. 13 is a perspective view of an alternate embodiment of a connecting apparatus connecting two longitudinal rods.

In an alternate embodiment illustrated in FIG. 13, a rod connector device is provided having a integral transverse rod or connective beam 502 as in the embodiment of FIG. 4. However, this connector 500 is designed to be used with the connector 504 which is identical to clip 10E illustrated in FIG. 15 of pending patent application Ser. No. 08/856,916, filed May 15, 1997, the contents of which are incorporated herein by reference. This transverse connector system of FIG. 13 requires fewer components than the system of FIGS. 15 and 16 of application Ser. No. 08/856,916 because the connective beam 502 extends integrally from one of the connecting devices. When assembled, semi-circular beam 502 lies in a plane parallel (and above as viewed in FIG. 13) to the plane of the longitudinal spinal rods 12 and 14. The semi-circular beam (rod) 502, however produces a lower profile than a system having a transverse circular rod. Connector 506 has arms 508, 510 and is clamped onto the longitudinal rod in the same manner as connector 32 of FIGS. 1–9.

Although the apparatus disclosed herein has been described with respect to preferred embodiments, it is apparent that modifications and changes can be made thereto without departing from the spirit and scope of the invention as defined by the claims.

What is claimed is:

1. Apparatus for connecting first and second spaced apart spinal rods to one another comprising:
   a) a first connector configured to engage the first spinal rod at a location along the length thereof and including an elongated connective beam extending in a direction transverse to the first spinal rod;
   b) a second connector configured to engage the second spinal rod and including a reception portion projecting in a direction transverse to the second spinal rod and defining a linear channel for receiving the elongated connective beam of the first connector; and
   c) a locking member dimensioned and configured to linearly engage the channel and secure the longitudinal position of said elongated connective beam with respect to said second connector.

2. Apparatus as recited in claim 1, wherein the first connector includes a pair of opposed spaced apart arcuate engaging members configured to engage the first spinal rod and the second connector includes a pair of opposed spaced apart arcuate engaging members configured to engage the second spinal rod.

3. Apparatus as recited in claim 2, wherein the first connector defines a yoke portion which includes a pair of opposed spaced apart arms, each of the spaced apart arms having an arcuate engaging member associated therewith.

4. Apparatus as recited in claim 2, wherein the second connector defines a yoke portion which includes a pair of opposed spaced apart arms, each of the spaced apart arms having an arcuate engaging member associated therewith.

5. Apparatus as recited in claim 1, wherein the linear channel is defined by a base portion having a planar surface and a pair of opposed spaced apart upstanding walls.

6. Apparatus as recited in claim 5, wherein the elongated connective beam has a semi-circular transverse cross-section, a lower surface thereof being planar and an upper surface thereof being curved.

7. Apparatus as recited in claim 6, wherein the planar lower surface of the elongated connective beam is configured to contact the planar surface of the base portion of the linear channel.

8. Apparatus as recited in claim 6, wherein the locking member includes a lower surface having a hemi-cylindrical channel for accommodating the upper surface of the elongated connective beam.

9. Apparatus as recited in claim 5, wherein the locking member includes an upper body portion having opposed leading and trailing ends, opposed lateral sides, and a pair of retention ports located on each of the lateral sides, the retention ports on each lateral side being spaced from one another at locations adjacent the leading and trailing ends of the upper body portion.

10. Apparatus as recited in claim 9, wherein the opposed spaced apart upstanding walls of the channel each include an interior surface having a pair of spaced apart locking tabs for engaging a pair of corresponding spaced apart retention ports of the locking member.

11. Apparatus as recited in claim 5, wherein the locking member includes a lower body portion defining a pair of laterally opposed tapered wedges.

12. Apparatus as recited in claim 11, wherein the opposed spaced apart upstanding walls of the channel each include an interior surface having a pair of tapered slots for receiving and engaging the pair of laterally opposed tapered wedges.

13. A connecting member for connecting a transverse spinal rod to a longitudinal spinal rod comprising a base portion, a pair of spaced apart arcuate engaging members extending in a first direction from the base portion to engage the longitudinal spinal rod, and a pair of upstanding walls extending in a direction transverse to the first direction and forming a channel therebetween to receive the transverse spinal rod.

14. A connecting member as recited in claim 13, wherein the channel is configured to linearly receive a locking member to secure the transverse spinal rod within the channel.

15. A connecting member as recited in claim 14, wherein the channel has a base portion having a planar surface to receive a lower planar surface of the transverse spinal rod.

16. A connecting member as recited in claim 14, wherein the upstanding walls of the channel each include an interior surface having a pair of spaced apart locking tabs for engaging a pair of corresponding spaced apart retention ports of the locking member.

17. A connecting member as recited in claim 16, wherein the opposed spaced apart upstanding walls of the channel each include an interior surface having a pair of tapered slots for engaging the pair of laterally opposed tapered wedges.

18. A connecting member for connecting a transverse spinal rod to a longitudinal spinal rod comprising a base portion, a pair of upstanding walls extending from the base portion forming a channel to receive a transverse spinal rod in a first plane, and a pair of arcuate engaging members extending from the base portion to engage the longitudinal rod in substantially the same plane as the first plane.

19. A connecting member as recited in claim 18, wherein the bottom surface of the base portion of the channel is planar and configured to a contact a planar lower surface of the transverse rod.

20. A connecting member as recited in claim 18, wherein the channel is configured to linearly receive a locking member to retain the transverse spinal rod within the channel.

21. A connecting member as recited in claim 20, wherein the upstanding walls of the channel each include an interior surface having a pair of spaced apart locking tabs for engaging a pair of corresponding spaced apart retention ports of the locking member.

22. A connecting member as recited in claim 21, wherein the opposed spaced apart upstanding walls of the channel each include an interior surface having a pair of tapered slots for engaging the pair of laterally opposed tapered wedges.

23. A connecting member as recited in claim 18, wherein the arcuate engaging members are oppositely facing mirror images of one another.

24. A spinal stabilization system comprising: a connecting member for connecting a transverse spinal rod to a longitudinal spinal rod, at least one fastener for connecting the longitudinal rod to the spine, the connecting member including first and second spaced apart engaging members configured to engage the longitudinal rod, the engaging members spaced apart from one another a sufficient distance to accommodate the fastener therebetween.

25. A connecting member as recited in claim 24, further comprising an elongated connective beam extending integrally from the connecting member.

26. System for spinal stabilization comprising:
a) a first elongated spinal rod;
b) a second elongated spinal rod;
c) at least one fastening device for securing the first elongated spinal rod to a first side of the spinous process;
d) at least one fastening device for securing the second elongated spinal rod to a second side of the spinous process in spaced relationship to the first spinal rod;
e) a first connector configured to engage the first spinal rod at a location along the length thereof and including an elongated connective beam having an axis extending in a direction transverse to the first spinal rod;
f) a second connector configured to engage the second spinal rod at a location adjacent the first connector and including a reception portion projecting in a direction transverse to the second spinal rod and defining a linear channel for receiving the elongated connective beam of the first connector; and
g) a locking member dimensioned and configured to linearly engage the channel along the axis of the connective beam and secure the longitudinal position of the connective beam with respect to the second connector so as to transversely connect the first and second spinal rods to one another.

27. System as recited in claim 26, wherein the first and second fastening a devices are selected from the group consisting of hooks and screws.

28. System as recited in claim 27, wherein the hooks and screws each include linear reception channels for accommodating the spinal rods, and the hooks and screws are secured to the spinal rods by respective locking members which linearly engage the reception channels of the hooks and screws along the longitudinal axis of the spinal rod associated therewith.

29. System as recited in claim 26, wherein the first connector includes a pair of opposed spaced apart arcuate engaging members configured to engage the first spinal rod and the second connector includes a pair of opposed spaced apart arcuate engaging members configured to engage the second spinal rod.

30. System as recited in claim 29, wherein the first connector defines a yoke portion which includes a pair of opposed spaced apart arms, each of the spaced apart arms having an arcuate engaging member associated therewith.

31. Apparatus as recited in claim 29, wherein the second connector defines a yoke portion which includes a pair of opposed spaced apart arms, each of the spaced apart arms having an arcuate engaging member associated therewith.

* * * * *